United States Patent

Maincent et al.

[11] Patent Number: 5,308,624
[45] Date of Patent: May 3, 1994

[54] OPHTHALMIC PRODUCT

[75] Inventors: Philippe Maincent; Laurent Marchal-Heussler, both of Nancy; Daniel Sirdat, Strasbourg, all of France

[73] Assignee: Laboratorios Cusi, S.A., El Masnou, Spain

[21] Appl. No.: 677,531

[22] Filed: Mar. 29, 1991

[30] Foreign Application Priority Data

Apr. 3, 1990 [FR] France ............... 90 04491

[51] Int. Cl.$^5$ ............... A61K 9/51
[52] U.S. Cl. ............... 424/427; 424/401; 424/428; 424/489; 424/490; 424/497; 424/502; 514/963
[58] Field of Search ............... 424/427, 428, 490, 489, 424/497, 502; 514/963

[56] References Cited

U.S. PATENT DOCUMENTS 4,795,436 1/1989 Robinson ............... 514/963
4,997,652 3/1991 Wong ............... 424/427
5,049,322 9/1991 Devissaguet et al. ............... 424/490

FOREIGN PATENT DOCUMENTS 0274961 7/1988 European Pat. Off. .
0322319 6/1989 European Pat. Off. .
3722837 7/1987 Fed. Rep. of Germany .

Primary Examiner—Thurman K. Page
Assistant Examiner—James M. Spear
Attorney, Agent, or Firm—Darby & Darby

[57] ABSTRACT

Ophthalmic product comprising nanocapsules, process for preparing it and application of the nanocapsules.

The present invention relates to an ophthalmic product comprising nanocapsules, characterized by a central core of lipid nature surrounded by a polymeric membrane capable of adhering to biological tissues.

The present invention also relates to its preparation and to the application of the nanocapsules for ophthalmic use.

17 Claims, 2 Drawing Sheets

OPHTHALMIC PRODUCT

The present invention relates to a novel product intended for ophthalmic use.

Eye diseases are generally treated by instilling one or more drops of collyrium on the cornea at the level of the lower eyelid. The majority of collyria are in the form of an aqueous solution containing the active principle in dissolved form. The cornea proper is covered by a lipophilic multi-layer epithelium having the function of a barrier for foreign bodies such as collyria so that during administration the collyria mix with the lachrymal fluid which permanently covers the eye and are very rapidly eliminated towards the nasal fossae. It is thought that the time during which the collyria act does not exceed one to two minutes and that only 10% of the quantity of active principle instilled exerts a therapeutic action.

Collyria in the form of an aqueous solution are thus not entirely satisfactory and have to be administered several times a day to exert a minimal therapeutic effect.

Various contrivances of galenic formulation have been envisaged to increase the fraction of medicament penetrating the eye: increasing the viscosity of the solutions, manufacturing optionally biodegradable inserts placed between the eye and the eyelid, the wearing of contact lenses, etc. All these systems have enabled the therapeutic effect of the medicoments to be increased, but none of them has yet replaced aqueous collyria because of blurring of vision and the uncomfortable sensation brought about by these systems in patients.

The present invention enables the problems mentioned above to be solved. In fact, the present invention relates to a novel ophthalmic product comprising nanocapsules and enabling the intraocular penetration of the medicoments to be increased considerably, in an unexpected manner. Within the context of the present invention, the term "ophthalmic product" designates not only a collyrium, namely products intended to be deposited on the outside of the eye at the level of the eyelids, but also products intended to be administered in the interior of the eye, namely in particular below the sclerotic conjunctiva or even in the vitreous humour. Advantageously, it has been possible to carry out such internal administration by means of appropriate syringes with the ophthalmic products of the present invention. The said ophthalmic products may furthermore be injected not directly into the eye but into the peri-ocular region (injections intended for the palpebral-oculo-orbital region, ocular surroundings and paths of visual projection and conduction).

The invention is further illustrated below by reference to the following drawings, the purpose of which is not to limit the scope of the invention

BRIEF DESCRIPTION OF THE DRAWINGS

FIG. 2 is a graph of chronological evolution of the intra-ocular pressure after instillation of commercial collyrium (diamonds) and nanocapsules of the present invention (squares) containing carteolol.

Figure 1:
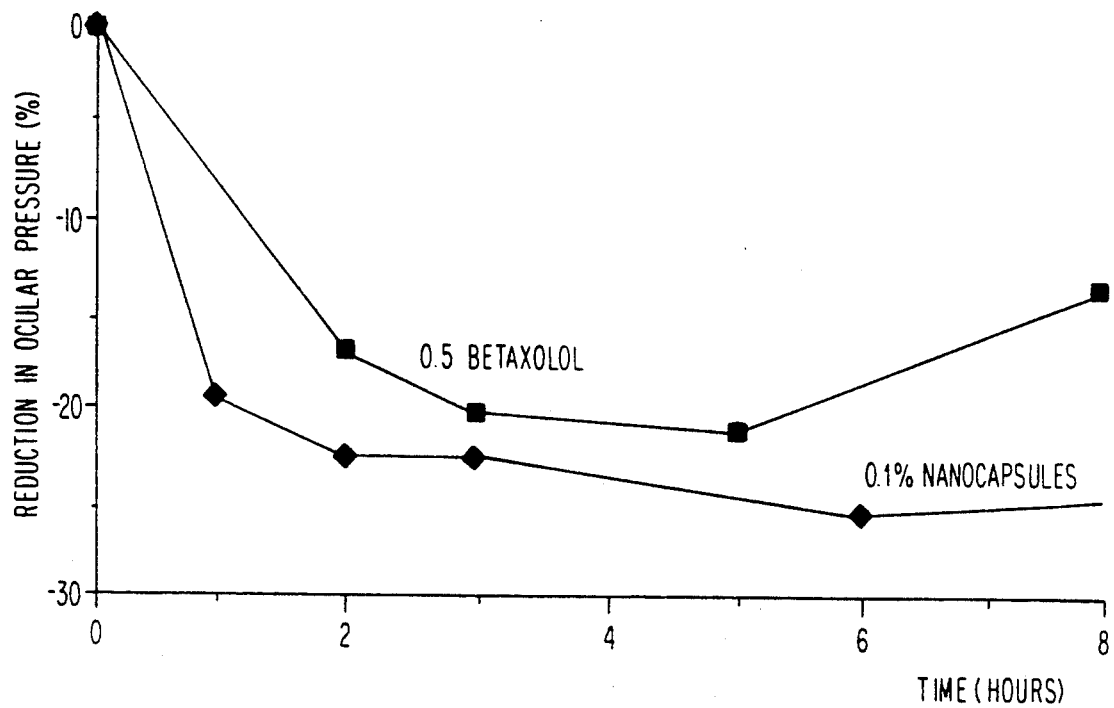
FIG. 1 is a graph of chronological evolution of the intra-ocular pressure after instillation of commercial collyrium (squares) and nanocapsules of the present invention (diamonds) containing betaxolol.
Figure 2:
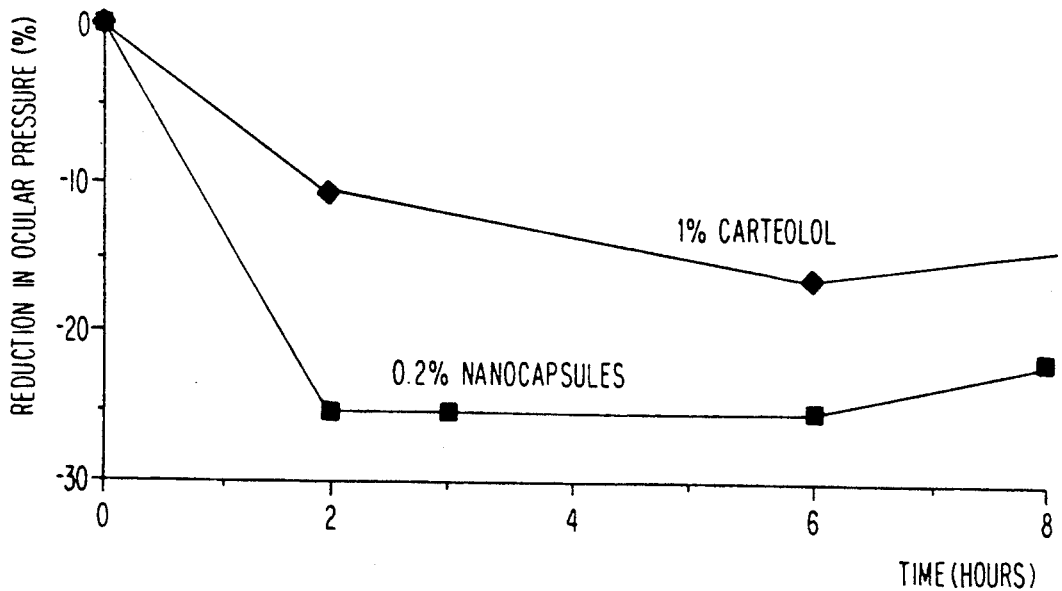
FIG. 2 is a graph of chronological evolution of the intra-ocular pressure after instillation of commercial collyrium (squares) and nanocapsules of the present invention (diamonds) containing betaxolol.

Preferably, in accordance with the present invention, the nanocapsules are vesicular structures formed by a central core of oily or lipid nature surrounded by a fine polymeric membrane capable of adhering to biological tissues. These nanocapsules have a diameter of betxveen 100 and 5000 nm, preferably between 200 and 500 nm. The nanocapsules of the present invention may enable cosmetics intended for ophthalmic use to be produced, such as products enabling the colour of the iris to be modified. The nanocapsules of the present invention may also carry markers (gamma emitters), tracers or colouring agents, in particular intended to display the condition of the haemato-ocular barriers.

However, according to the present invention the said nanocapsules are preferably intended to carry one or more medicinal active principles. This will in particular be for the treatment of the most conunon eye diseases, such as intraocular hypertension or glaucoma, inflaminations, allergies or infections. It is for this reason that the active principle is preferably chosen from anti-hypertensive agents such as betaxolol (ALCON Laboratories, Ft. Worth, Texas, USA) or carteolol (OTSUKA Laboratory, Japan), anti-inflammatory agents such as indomethacin, anti-allergic agents or antibiotics such as tetracyclines. The ophthalmic products of the present invention also enable dry-eye syndrome to be treated, either by carrying a substance intended to stimulate the formation of artificial tears or by themselves creating a medium providing a substitute for insufficient tears.

Furthermore, it is known that those suffering from AIDS or other viral diseases very frequently become blind, in a manner which is inescapable, because of the inadequacy of conventional collyria. It is f or this reason that in accordance with the present invention the active principle carried by the nanocapsules is preferably chosen from the anti-viral agents: these are in particular acyclovir or iododeoxy uridine; and the ocular effects of viral diseases can thus be effectively checked. It goes without saying that in accordance with the present invention a plurality of active principles can be used in combination in the said nanocapsules. In fact, all molecules, whether of lipophilic or hydrophilic nature, can be incorporated in the nanocapsules of the present invention. This constitutes a considerable additional advantage, since it is known that certain active principles necessary however for the prevention or cure of particular eye diseases cannot, because of their lipophilic nature, be incorporated in conventional collyria.

This advantage results from the conventional process for preparing the nanocapsules, as appears for example in EP 274 961, and in the following steps:
 (a) the active principle or principles are dissolved in their non-ionized form in a lipophilic solvent, such as an oil;
 (b) the product obtained from step (a) is mixed with an organic solvent in which a polymer has previously been dissolved;

(c) the product obtained from step (b) is added to an aqueous solution containing a surfactant agent, with stirring;

(d) the organic solvent and where appropriate some of the water are evaporated from the product obtained from step (c) in order to obtain the desired concentration of active principle.

Preferably, in accordance with the present invention, before step (a), the salt of the active principle is converted to the non-ionized form of the said active principle. This conversion may be carried out in conventional manner but, preferably, in accordance with the present invention the active principle is dissolved in distilled water, the pH of this aqueous phase is adjusted to pKa−2 if the active principle is an acid or pKa+2 where the active principle is a base; the active principle then passes into the non-ionized form, precipitates and can be extracted by means of an appropriate solvent.

In the course of step (a), there is preferably used as the lipophilic solvent Mygliol 812 ®. The polymer used in step (b) of the process of the present invention is preferably polyepsiloncaprolactone, but other appropriate polymers may be used (polyacrylic derivatives, etc.). Finally, various surfactants may be used in the course of step (c); one may for example make use of Pluronic F68 ®.

The result of the said preparation process is that the ophthalmic products of the present invention supply the active principle in its non-ionized form, insoluble in water and thus insoluble in a conventional collyrium. Furthermore, the fact that the active principle is dissolved in an oil allows it to be protected from the action of the lachrymal fluid which could re-ionize it and thus cause it to lose its lipophilic nature. This non-ionized form is advantageously retained by the lipophilic epithelium to reach the aqueous stroma. Once in the said stroma, the active principle can take up its hydrophilic form again. In fact, at the pH of the stroma (approximately 7) the active principle takes up its ionized form again and again becomes soluble in aqueous medium, allowing it to diffuse across the stroma. The aqueous stroma constitutes approximately 9/10 of the thickness of the cornea and ends in a unilayer endothelium which is very permeable to all substances and can thus easily be crossed by the ionized active principle.

The results obtained following the experiments carried out with the ophthalmic products of the present invention are surprising: for a considerably increased therapeutic effect which lasts longer in time, the quantities of active principle used are approximately at most a fifth of that of commercially available collyria. At the same time, a decrease in the undesirable side effects is observed.

Consequently, thanks to the ophthalmic products of the present invention, it will be possible to:
decrease the number of instillations or injections at the time of treating patients
use certain active principles in non-toxic doses, such as atenolol.

The present invention also relates to the application of nanocapsules for preparing ophthalmic products, namely on the one hand products intended for tonical ocular or peri-ocular use, such as collyria, and on the other hand products intended for systemic ocular or peri-ocular administration. In fact, in accordance with the present invention it is possible to make use of all the means of administration used in ophthalmology, such as sub-conjunctival or intra-vitreous administration. Thus, shadowgraph studies carried out during an intra-vitreous administration of the nanocapsules of the present invention show that the said capsules remain in the vitreous humour for at least 48 to 72 hours. Given that currently at least two intra-vitreous administrations per day are required to treat someone suffering from AIDS, one can imagine the scope of progress enabled by the ophthalmic products of the present invention, since the number of intra-vitreous injections required is considerably reduced.

The present invention is illustrated by the following non-restrictive examples.

EXAMPLE 1: Process for preparing the ophthalmic products of the present invention.

1- 1 Case with betaxolol

The active principle is dissolved in water.

Then, the pH of this aqueous phase is adjusted to (pKa+2) with NaOH 1N.

The active principle takes on the non-ionized form and precipitates.

The active principle is then extracted in a chloroform phase.

Finally, after separation by decanting, the chloroform phase is dried and the active principle crystallizes.

0.005 g of non-ionized betaxolol are dissolved in 0.5 ml of lipophilic excipient (Mygliol 812 ®).

0.125 g of non-ionized betaxolol are dissolved in 0.5 ml of lipophilic excipient (Mygliol 812 ®).

Then, the Mygliol 812 ® containing the betaxolol is mixed with the acetone containing the polycaprolactone, with stirring (300 rpm).

The acetone containing the polycaprolactone, the Mygliol 812 ®, and the betaxolol is then added with magnetic stirring (500 rpm) to 50 ml of water at pH 7 containing 0.125 g of surfactant (Pluronic F 66 ®).

Homogenization is carried out for 5 minutes. Then the suspension formed is evaporated in vacuo until a final volume of 5 ml is reached.

| Polycaprolactone | 2.5 g % |
|---|---|
| Pluronic F 68 ® | 2.5 g % |
| Mygliol 812 ® | 10 ml |
| Non-ionized betaxolol | 0.1 g % |

The pH is readjusted to 7 if necessary by NAOH 0.1N and 0.01 g of preservative (benzalkonium chloride) is added.

1-2 Case with carteolol

The active principle is dissolved in water.

Then, the pH of this aqueous phase is adjusted to (pKa+2) with NAOH 1N.

The active principle takes on the non-ionized form and precipitates.

The active principle is then extracted in a chloroform phase.

Finally, after separation by decanting, the chloroform phase is dried and the active principle crystallizes.

0.01 g of non-ionized carteolol are dissolved in 0.5 ml of lipophilic excipient (Tio5 ® oil).

0.125 g of polyepsiloncaprolactone are dissolved in 20 ml of organic solvent (acetone) by ultrasound action for 5 minutes.

The oil containing the carteolol is mixed with the acetone containing the polycaprolactone, with stirring (300 rpm).

Then, the acetone containing the polycaprolactone, the oil and the carteolol is added with magnetic stirring (500 rpm) to 50 ml of water (pH 7) containing 0.125 g of surfactant (Pluronic F 68 ®).

Homogenization is carried out for 5 minutes. Finally, the suspension formed is evaporated in vacuo until a final volume of 5 ml is reached. The following concentrations result:

| Polycaprolactone | 2.5 g % |
|---|---|
| Pluronic F 68 ® | 2.5 g % |
| Tio5 ® | 10 ml |
| Non-ionized carteolol | 0.2 g % |

The pH is readjusted to 7 if necessary with NAOH 0.1N and 0.01 g of preservative (benzalkonium chloride) is added.

1-3 Case with indium oxinate (radioactive product provided by the C.E.A. (French Atomic Energy Commission), Saclay, France)

1 ml of indium oxinate solution is mixed with 1 ml of Tio5 ® oil; the mixture is stirred for 15 minutes.

The mixture is centrifuged at 3000 rpm for 5 minutes.

0. 5 ml of Tio5 ® oil are then sampled and mixed by magnetic stirring (300 rpm) with 20 ml of organic solvent (acetone) containing 0.125 g of polycaprolactone previously dissolved by the action of ultrasound for 5 minutes.

Then, the acetone containing the polycaprolactone, the oil and the indium oxinate is added with magnetic stirring (500 rpm) to 50 ml of water at pH 7 containing 0.125 g of surfactant (Pluronic F 68 ®).

Homogenization is carried out for 5 minutes. Finally, the suspension formed is evaporated in vacuo until a final volume of 5 ml is reached.

EXAMPLE 2: Tests in vivo on rabbits.

These tests were carried out with the aid of two beta-blockers used in the treatment of intraocular hypertension or glaucoma. In order to reduce the intraocular hypertension, these molecules have to penetrate the eyeball. The penetration of the medicament into the eye, after instillation at the level of the conjunctival sac, is a direct function of the time it remains in contact with the eye. This contact time is very small with the collyria currently commercially available. When the same product is incorporated in the ophthalmic product of the present invention, it remains in contact with the eye for much longer. This increase in the time of local residence is demonstrated by gamma-shadowgraph studies and by measuring the therapeutic effect.

2-1 Therapeutic effect

The therapeutic effect is measured directly in the rabbit which was given glaucoma (by injecting chymotrypsin into the eye) with the aid of an aplanatic ionometer. The two active principles tested are currently used in the treatment of glaucoma. These are: betaxolol (Betoptic ®, Alcon Laboratories, Kaysersberg, France) and carteolol (Carteol ®, Chauvin-Blache Laboratories, France). The results obtained are shown in the FIGS. (1 and 2). These FIGURES show the chronological evolution of intraocular pressure after instillation of the commercial collyrium containing either 0.5% betaxolol or 1% carteolol and the ophthalmic products of the present invention containing either 0.1% betaxolol or 0.2% carteolol.

With a concentration only one fifth as strong of active principle by comparison with the two commercially available collyria, the ophthalmic products of the present invention increase significantly (test of t, $p<0.01$) and for an extended period the decrease in intraocular pressure. Moreover, the use of a lower concentration of active principle in the ophthalmic products of the present invention allows a reduction in the undesirable side effects encountered when 90% of the product passes into general circulation (cardiac, respiratory and neurological effects of current collyria).

2-2 Study of secondary cardiovascular effects

Figure 3:
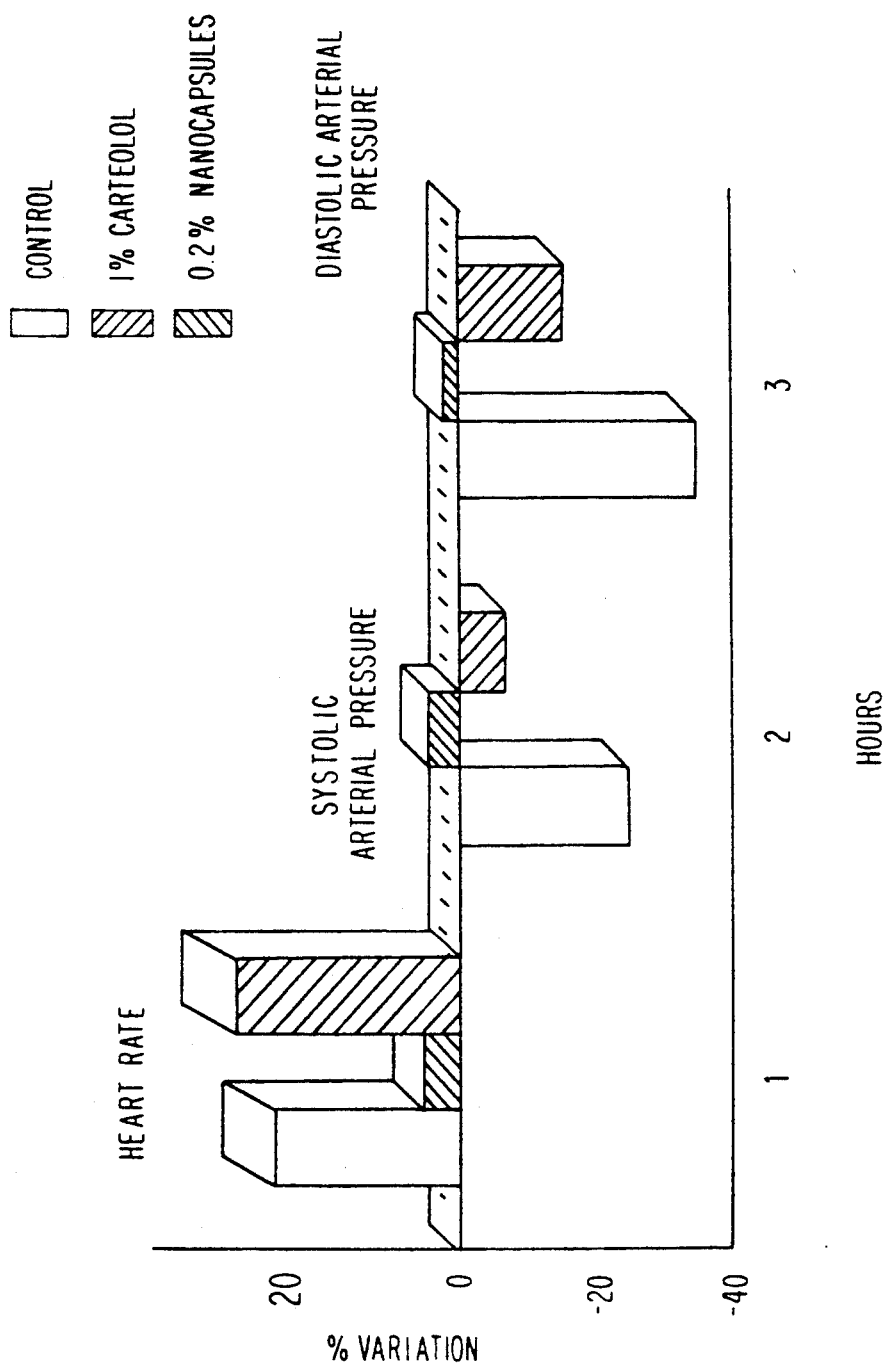
FIG. 3 is a bar graph depicting variation in responses of the cardiovascular system to stimulation with isoprenaline under normal conditions (control) 90 minutes after instillation of 1% Carteol ® (carteolol 1%) and 90% minutes after instillation of the ophthalmic product of the present invention (nanocapsules containing 0.2% carteolol).

In order to demonstrate the secondary cardiovascular effects following instillation of the beta-blocker collyria, the cardiovascular system of the rabbit is stimulated by a single administration of a dose of isoprenaline ($2.5 \; \mu g/kg$). The result of this administration is an increase in the heart rate and a decrease in arterial pressure. After instillation of the commercially available collyrium (Carteol ® 1%), the same injection of isoprenaline no longer modifies the heart rate and increases the arterial pressure. This leads to beta-blocking of the general cardiovascular system and may be the cause of the side effects such as severe cardiac disorders and subsequently cerebro-vascular illnesses. Under the same conditions, the instillation of the ophthalmic products of the present invention containing carteolol at a dose of only a fifth (0.2%) significantly reduces beta-blocking in the general cardiovascular system while having a therapeutic action superior to that of the commercially available collyrium. Thus, the incidence of undesirable illnesses is reduced to a very considerable extent. These results are shown in diagrammatic form in FIG. 3.

2-3 Gamma-shadowgraph study

The ophthalmic products of the present invention are marked with the aid of a gamma emitter, indium oxinate, and monitored by a gamma camera after instillation into the eye of the rabbit. At the same time, the indium solution simulating the collyrium (control) is instilled in the other eye and monitored by the same camera. The results obtained show that after 5 minutes there is no more than 40% of initial radioactivity in the eye receiving the indium solution, while at the end of 20 minutes 80% of the radioactivity administered at the outset is still present in front of the eye receiving the ophthalmic products of the present invention.

In conclusion, the ophthalmic products of the present invention allow the contact time of a medicament in the eye to be extended and to deliver the active principle in the non-ionized form, which penetrates across the cornea better. They thus significantly improve its efficacity. The use of polymers already used in other sectors of health care and considered as biocompatible provides a basic guarantee of the absence of toxicity of the nanocapsules. On the other hand, their tolerance in the rabbit was satisfactory. In time, all the active principles used in ophthalmology (antibiotics, anti-viral agents, anti-inflammatory agents, etc.) are capable of being incorporated into the ophthalmic products of the present invention and of thus greatly increasing their efficacity, as well as their duration of action, and consequently greatly reducing their side effects.

We claim:

1. Composition for ophthalmic use comprising:

(a) nanocapsules comprising a vesicle comprising a lipid or oily core surrounded by a polymeric membrane said polymeric membrane comprising a polymer insoluble in water but soluble in an organic solvent, said nanocapsules releasably containing an active ingredient in nonionized form said active ingredient being dissolved within said core and assuming an ionized form when delivered to its use point; and (b) physiologically acceptable carrier or vehicle.

2. Composition for ophthalmic use comprising:

(a) nanocapsules comprising a vesicle comprising a lipid or oily core surrounded by a caprolactone polymeric membrane said polymeric membrane comprising a polymer insoluble in water but soluble in an organic solvent, said nanocapsules releasably containing an active ingredient in nonionized form said active ingredient being dissolved within said core and assuming an ionized form when delivered to its use point; and (b) a physiologically acceptable carrier or vehicle.

3. Composition according to claim 1 wherein the nanocapsules have a diameter within the range from about 200 to about 500 nm.

4. Composition according to claim 1 wherein said active ingredient is selected from the group consisting of medicaments and combinations thereof.

5. Composition according to claim 1 wherein said active ingredient is a cosmetic.

6. Composition according to claim 4 wherein said medicament is an antiviral agent.

7. Composition according to claim 6 wherein said antiviral agent is selected from the group consisting of acyclovir and iododeoxyuridine.

8. Composition according to claim 4 wherein said medicament is an antibiotic.

9. Composition according to claim 8 wherein said antibiotic is tetracycline.

10. Composition according to claim 4 wherein said medicament is an anti-hypertensive agent.

11. Composition according to claim 10 wherein said anti-hypertensive agent is selected from the group consisting of betaxolol and carteolol.

12. Process for preparing a composition according to claim 1 comprising the steps of:

(a) dissolving the active ingredient in nonionized form in a lipophilic solvent;

(b) mixing the solution obtained in step (a) with a solution of a caprolactone polymer in an organic solvent;

(c) adding the mixture obtained in step (b) to an aqueous solution containing an emulsifying agent, under stirring;

(d) evaporating the organic solvent and recovering said nanocapsules.

13. Process according to claim 12 wherein said step (d) further comprises evaporating at least a portion of the water contained in said aqueous solution.

14. Process according to claim 12 further comprising the step of converting said active ingredient to nonionized form prior to said step (a).

15. Composition according to claim 1 said composition being in collyrium form.

16. Composition according to claim 1 wherein said nanocapsules and said carrier or vehicle are suitable for intraocular administration.

17. Composition according to claim 1 wherein said nanocapsules and said carrier or vehicle are suitable for periocular administration.

* * * * *